(12) United States Patent
Johnson et al.

(10) Patent No.: US 6,899,724 B1
(45) Date of Patent: May 31, 2005

(54) CIRCULAR BULB PORTABLE FEET TANNING DEVICE

(76) Inventors: William Johnson, 4040 42nd St., Sarasota, FL (US) 34235; Colleen Johnson, 4040 42nd St., Sarasota, FL (US) 34235

(*) Notice: Subject to any disclaimer, the term of this patent is extended or adjusted under 35 U.S.C. 154(b) by 0 days.

(21) Appl. No.: 10/419,619

(22) Filed: Apr. 21, 2003

(51) Int. Cl.$^7$ ................................................ A61N 5/06
(52) U.S. Cl. ......................................... 607/94; 607/90
(58) Field of Search .................... 607/88–94; 250/504

(56) References Cited

U.S. PATENT DOCUMENTS

| | | | |
|---|---|---|---|
| 1,280,857 A | 10/1918 | Ruiter | |
| 1,337,798 A | 4/1920 | Ruiter | |
| 1,660,794 A | 2/1928 | Hudson | |
| 1,718,770 A | 6/1929 | Zublin | |
| 2,054,332 A | 9/1936 | Lower et al. | |
| 2,311,415 A | 2/1943 | Rouat | |
| 2,444,379 A | 6/1948 | Sexton | |
| 3,101,716 A | 8/1963 | Cornell, Jr. | |
| 3,531,687 A * | 9/1970 | Greber | .................... 315/309 |
| 4,287,554 A | 9/1981 | Wolff | |
| 5,466,248 A | 11/1995 | Whitson-Newman | |
| 5,565,685 A * | 10/1996 | Czako et al. | ........... 250/504 R |
| 6,139,568 A * | 10/2000 | Doty | .......................... 607/91 |
| 6,273,906 B1 | 8/2001 | Swanson | |
| 6,309,366 B1 | 10/2001 | Maxwell | |
| 6,676,687 B2 * | 1/2004 | Stoppler | ..................... 607/94 |

* cited by examiner

*Primary Examiner*—Roy D Gibson
*Assistant Examiner*—Henry M Johnson, III
(74) *Attorney, Agent, or Firm*—Michael I. Kroll (57) ABSTRACT

The present invention discloses a portable foot tanning device The foot tanning device is comprised of a housing having an opening leading into a compartment comprised of a transparent receptacle that protects the user's feet from the lamp. The housing also has external controls for setting the time duration of the tanning session. When the device is turned on a fan comes on to regulate the internal temperature. The feet receptacle is releasably attached to the interior of the device and is accessible through the underside of the device which is open thereby a user can selectively remove and clean the feet receptacle between tanning sessions. The ultraviolet lamp encircles the feet receptacle providing an even tan of the inserted appendages and is easily replacable through the bottom of the device.

13 Claims, 7 Drawing Sheets

CIRCULAR BULB PORTABLE FEET TANNING DEVICE

BACKGROUND OF THE INVENTION

1. Field of the Invention

The present invention relates generally to tanning devices and more specifically to a foot tanning device. The foot tanning device is comprised of a housing having an aperture for the insertion therein of at least one foot wherein said housing having a timer and a light source providing ultraviolet light within said device provides means whereby a user can selectively set a time duration for tanning the enclosed appendage.

2. Description of the Prior Art

There are other devices designed for tanning. Typical of these is U.S. Pat. No. 1,280,857 issued to V. L. Ruiter on Oct. 8, 1918.

Another patent was issued to V. L. Ruiter on Apr. 20, 1920 as U.S. Pat. No. 1,337,798. Yet another U.S. Pat. No. 1,660,794 was issued to W. Hudson on Feb. 28, 1928 and still yet another was issued on Jun. 25, 1929 to M. N. Zublin as U.S. Pat. No. 1,718,770.

Another patent was issued to Lower, et al., on Sep. 15, 1936 as U.S. Pat. No. 2,054,332. Yet another U.S. Pat. No. 2,311,415 was issued to R. Rouat on Feb. 16, 1943. Another was issued to J. T. Sexton on Jun. 29, 1948 as U.S. Pat. No. 2,444,379 and still yet another was issued on Aug. 27, 1963 to E. S. Cornell, Jr. as U.S. Pat. No. 3,101,716.

Another patent was issued to F. Wolff on Sep. 1, 1981 as U.S. Pat. No. 4,287,554. Yet another U.S. Pat. No. 5,466,248 was issued to J. Whitson-Newman on Nov. 14, 1995. Another was issued to J. D. Swanson on Aug. 14, 2001 as U.S. Pat. No. 6,273,906 and still yet another was issued on Oct. 30, 2001 to R. E. Maxwell as U.S. Pat. No. 6,309,366.

This invention has for its object a novel and efficient therapeutic apparatus in which various diseases and ailments of the limbs of the body may be effectively treated by the application of an intense dry heat and strong rays of light.

One of the main objects of the invention is to provide an apparatus of the character stated by means of which the lower potion of the body may be subjected to the action of heat and light rays from all sides thereof so as to effectually penetrate the body so as to kill the disease germs and reduce inflammation and promote circulation.

In a therapeutic appliance for the purpose described, an inlet for alternating current, an inlet for direct current, a resistance element comprising a plurality of turns of resistance wire, and having one end connected to the direct current circuit and the other end connected to the alternating current circuit and a regular arm engaging said resistance and having a connection to both the direct current and alternating current line, whereby a portion of the resistance is included in the direct current circuit and another portion of said resistance in included in the alternating current circuit.

The invention provides a reducing and light treatment cabinet in which a person with a weak heart may be effectively treated. In actual practice, it is possible to keep a patient having a weak heart in a cabinet of the invention for twenty-eight minutes at a temperature of 120° F., whereas the patient can be kept only ten minutes in the common type of cabinet and only at a temperature of 80° F.

The invention relates to therapeutic lamps and particularly to one of a type designed for treating the feet and the lower portions of the legs of a patient. The principal objects of the invention are to provide an electric apparatus of this character so constructed that a great concentration of heat or light rays on the members being treated may be had with a relatively low consumption of electric current; one in which such heat or rays may be selectively directed against the feet from different directions and with different intensities without moving the feet and without the use of any complicated electrical apparatus; and one in which a comfortable support for the feet is provided, which may be manipulated by the patient to alter the position of the feet in the zone of heat as may be desired and arranged so that the entire area of the feet is exposed to the heat and light rays.

The invention relates to an electric bath and particularly to a bath in which the beneficial rays and heat from the electric element are reflected and projected onto and into the body of the bather while enclosed and reclining.

This invention relates to ray treating appliances of the portable character, and has for its primary aim to provide a therapeutic cabinet, designed to house ray lamps of the type known to be helpful in the treatment of skin diseases and that has unique structure for holding the member being treated in proper position with respect to said lamps.

This invention relates to apparatus for treating parts of the human body with radiation and in particular skin diseases of the feet and hands, for example, athlete's foot.

Apparatus for producing ultraviolet radiation, particularly a quick-tanning or therapeutic sunlamp, has a source of substantially uniform ultraviolet radiation, including at least two closely adjacent tubular low-pressure mercury lamps; an arrangement for intercepting at least the major percentage of wavelength bands of ultraviolet radiation below approximately 300 mm; and a reflector system cooperating with said source and defining at least one opening for the escape of ultraviolet radiation consisting essentially of the remaining wavelength band of ultraviolet radiation, said reflector system including for each of said lamps a trough-shaped reflector surrounding the lamp along an arc, and at least one intermediate portion between adjacent ones of said lamps and two lateral portions having zones which project forwardly of said intermediate portion and have forward edge portions defining said opening, the space between said lateral portions and forwardly of said intermediate portion being substantially unobstructed, and the source and reflector system cooperating to establish in the vicinity of the opening a high-density radiation field, the heat output of said lamps being sufficiently low so that the temperature in the region of said radiation field is below the range of discomfort of a person exposed to the field. The apparatus may include a mirror flanked by the lamps so that a user can enjoy the benefits of the ultraviolet radiation at no additional expenditure of time while looking into the mirror for other purposes.

A foot ghost ender comprised of a rounded steel shell having a front, a back, a left sidewall, a light sidewall, an open top, a closed bottom, an inner surface, and an outer surface. An aperture is formed in the right sidewall. An extension is integral with the open top. The extension has an open circular top. A plurality of tanning lamps are secured to the inner surface of the rounded steel shell. An adjustable foot rest is secured to the inner surface of the rounded steel shell. The device also contains a retractable power cord having a first end, and a second end. The first end is received through the aperture formed within the right sidewall of the rounded steel shell. A three-prong polarized plug secured to the first end. A control panel with adjustable timer is secured to the right sidewall of the rounded steel wall. The adjustable timer functions to turn the tanning lamps on and off.

A device for tanning the feet of athletes who develop tanned legs while wearing shorts to participate in outdoor activities. The tanning device also includes a fungicidal mechanism for killing foot funguses as well as a foot massaging mechanism for providing soothing vibrations to the feet while the user is receiving a tanning treatment.

A foot therapy device including a portable housing with an annular wall having an upper edge and defining a reservoir for retaining a volume of liquid to be used during foot therapy; a lid covering a given portion of the reservoir and secured to a continuous portion of the upper edge; and a liquid seal member disposed between the lid and the given upper edge portion.

While these tanning devices may be suitable for the purposes for which they were designed, they would not be as suitable for the purposes of the present invention, as hereinafter described.

SUMMARY OF THE PRESENT INVENTION

The present invention is a foot tanning device comprised of a housing having an aperture for the insertion of at least one foot wherein said housing having an ultraviolet light source provides means for tanning the feet.

Positioned within the housing is a substantially L-shaped receptacle forming a chamber for the feet having an aperture that circumferentially engages the housing aperture. The receptacle is manufactured from a transparent material protecting the feet from contact with the internal mechanisms while allowing the ultraviolet rays to pass through.

The receptacle is a removable feet compartment that engages the housing. Removing said compartment provides access to the internal components of the housing and allows for external cleaning of the receptacle.

Located on the exterior front wall of the housing is a control mechanism comprised of a timer electrically connected to a power source and lamp whereby the tanning device can be set to operate for a users selectable length of time. Also positioned within the wall of the housing is at least one vent providing means for the passage of air therethrough. A fan is preferably positioned on the interior side of the vent providing means for introducing a volume of ambient air to keep the interior temperature down. A second vent can also be provided as an egress for interior heat laden air that will also increase the volume of air exchanged by means of the vent fan.

The ultraviolet lamp is circular/elliptical in design circumferentially encompassing the transparent receptacle so that all skin areas of the feet and ankles will receive consistent amounts of ultraviolet light providing an even tan. The bulb is replaceably positioned within a socket having interior retaining members. The replacement of the bulb is easily accomplished by removal of the feet compartment providing access to the bulb and socket.

The transparent feet compartment is removable from the bottom of the assembly. An electro/mechanical interlock allows operation only when the feet compartment is properly installed. The transparent feet compartment having means for removal can be selectively cleaned by the user.

A primary object of the present invention is to provide a portable tanning device for feet.

Another object of the present invention is to provide a portable tanning device that is easy to use.

Yet another object of the present invention is to provide a portable tanning device that will eliminate undesirable tan lines around the ankles through selective use of the tanning device.

Still yet another object of the present invention is to provide a portable tanning device that can be easily cleaned.

A further object of the present invention is to provide a portable tanning device comprising a housing having an aperture for the insertion of feet.

A yet further object of the present invention is to provide a portable tanning device having a housing with external controls for operatively engaging the tanning device.

A still further object of the present invention is to provide a portable housing having an exteriorly positioned timer having electrical connection means with a power source and an interiorly positioned ultraviolet lamp whereby said lamp can be energized.

Another object of the present invention is to provide an exteriorly positioned timer whereby the operative duration of the tanning device can be selectively set.

Yet another object of the present invention is to provide a portable tanning device having a housing with at least one vent providing means for exchanging a volume of air between the interior housing and the exterior ambient air.

Still yet another object of the present invention is to provide mechanical means for increasing the volume of air exchanged between the interior and exterior of the tanning device.

A further object of the present invention is to provide a fan positioned on the interior of the tanning device providing means for increasing the volume of air exchanged between the interior and exterior of the tanning device.

A yet further object of the present invention is to provide a fan positioned on the interior of the tanning device in close proximity to the vent providing means for increasing the volumetric movement of air through said vent.

A still yet further object of the present invention is to provide a fan having electrical connection means with the timing device whereby operatively engaging the timing device operatively engages the fan.

Another object of the present invention is to optionally provide a portable tanning device having a second vent for increasing the volumetric exchange of air between the interior and exterior of the tanning device.

Yet another object of the present invention is to provide a portable tanning device having a removable feet compartment providing access to the interior of the tanning device.

Still yet another object of the present invention is to provide a portable tanning device having means for generating ultraviolet light rays.

A further object of the present invention is to provide a portable tanning device having an interiorly positioned ultraviolet light bulb.

A yet further object of the present invention is to provide a portable tanning device having a circular or elliptically shaped ultraviolet light bulb.

A still yet further object of the present invention is to provide a lamp socket for the insertion of the ultraviolet light bulb.

Another object of the present invention is to provide a lamp socket with electrical connection means with the timer wherein operatively engaging the timer energizes the lamp socket.

Yet another object of the present invention is to provide a tanning device having an ultraviolet light bulb that is easily replaceable.

Still yet another object of the present invention is to provide a portable tanning device having a circular or elliptical shaped ultraviolet light bulb that peripherially encompasses and is spaced apart from a compartment containing a user's feet.

A further object of the present invention is to provide a portable tanning device having an ultraviolet light bulb that can be selectively energized providing means for tanning a user's feet and ankles.

A yet further object of the present invention is to provide a portable tanning device having an interiorly positioned compartment for the insertion and containment of a user's feet during the operational tanning mode of the tanning device.

A still yet further object of the present invention is to provide an interiorly positioned compartment consisting of a receptacle having an aperture for the insertion of a user's feet.

Another object of the present invention is to provide a tanning device having a receptacle that provides means for a user to position their feet therein in a spaced apart position.

Yet another object of the present invention is to provide an interiorly positioned receptacle that is manufactured of a transparent material.

Still yet another object of the present invention is to provide an interiorly positioned receptacle that releasably engages the tanning device housing.

A further object of the present invention is to provide an electro/mechanical interlock that allows operation only when the feet compartment is properly installed.

A yet further object of the present invention is to provide an interiorly positioned receptacle that is easily removed through the tanning device housing aperture.

Additional objects of the present invention will appear as the description proceeds.

The present invention overcomes the shortcomings of the prior art devices by providing a feet tanning device comprised of a housing having an aperture for the insertion therein of feet wherein said housing having a light source selectively providing ultraviolet light provides means for said device to tan the feet and ankles.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

Figure 1:
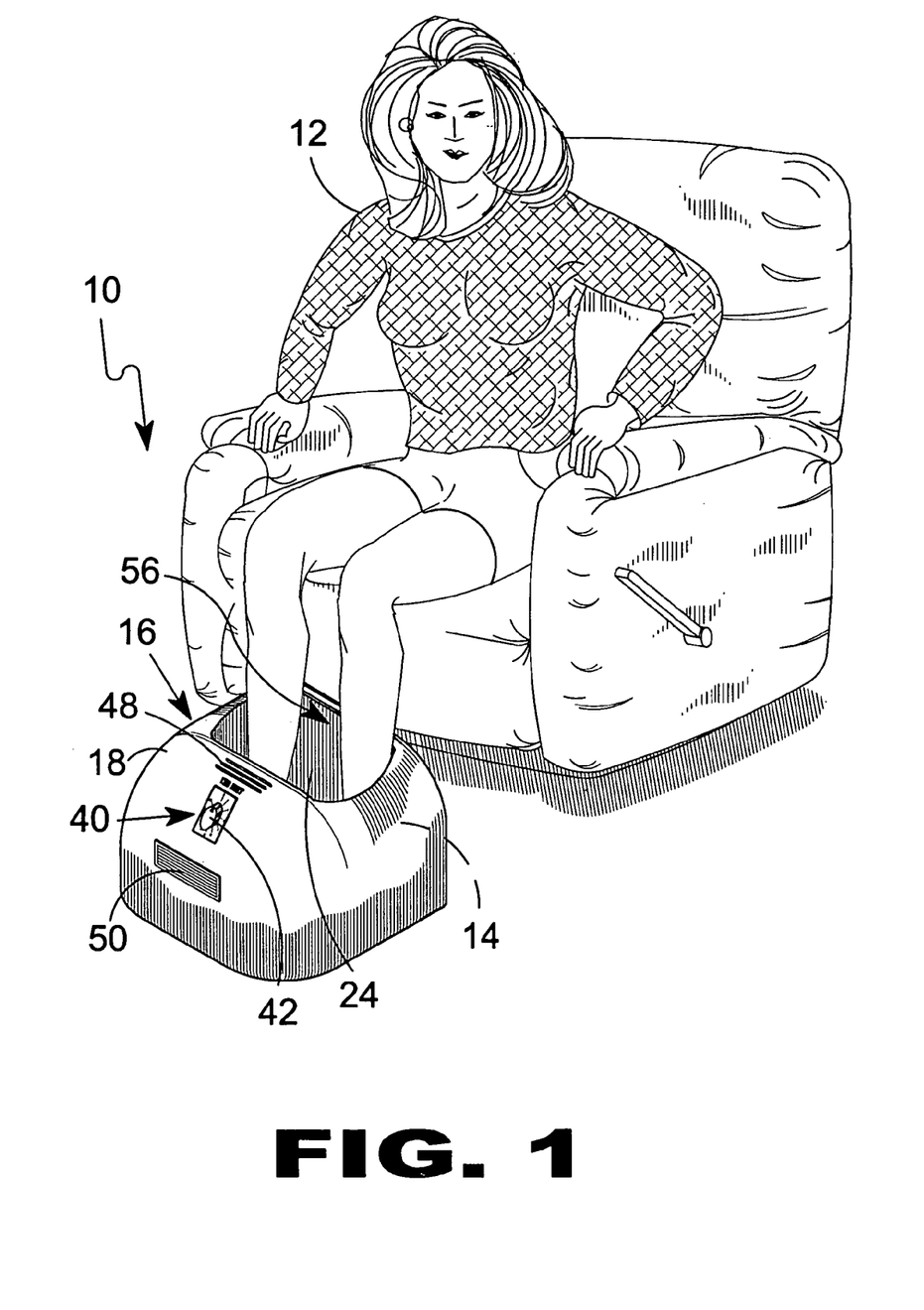
FIG. 1 is an illustrative view of the present invention.

Referring to FIG. 1, shown is a user of the portable tanning device of the present invention. The portable tanning device 10 has a housing 16 having an aperture 24 for the insertion of user's 12 feet 14. The tanning device 10 has exteriorly 18 positioned controls 40 for setting the duration of the tanning session by means of timer 42. There is also a vent 50 for increasing the volumetric input of air into the device and a vent 48 for removing the heated interior air. The housing also has a transparent receptacle 56 that can be removed for selective cleaning by releasing the fastening means used to mount the transparent receptacle 56 to housing 16.

There is also a vent 50 for increasing the volumetric input of air into the device and a vent 48 for venting the heated interior air. The housing 16 has aperture 24 providing access to transparent receptacle 56 having foot receptacle aperture 58 for the containment of a user's feet during a tanning session.

Figure 2:
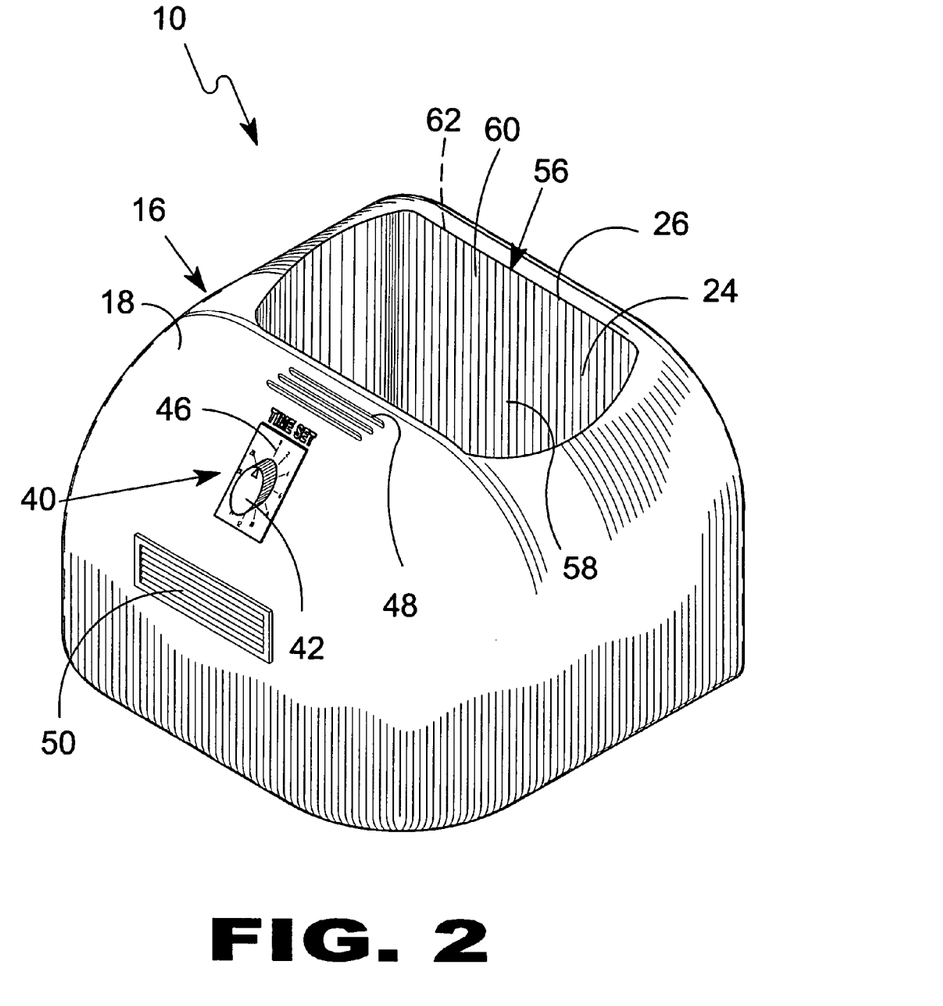
FIG. 2 is a perspective view of the portable tanning device of the present invention.

Referring to FIG. 2, shown is a perspective view of the portable tanning device 10 of the present invention. The tanning device 10 is comprised of a housing 16 having an aperture 24 bounded by rim 26 and an exterior surface 18 whereupon decorative elements or logos can be attached thereto. The housing 16 has control mechanism 40 whereby a user selects a time duration displayed as time graduations 46 using timer 42 which energizes the tanning device. Fan vent 50 provides a source of ambient air which is moved into the interior housing enclosure to remove excess heat through vent 48 during a tanning session. The user places their feet into transparent receptacle 56 through aperture 58 bounded by rim 62. The transparent receptacle 56 is accessed through housing aperture 24 bounded by aperture rim 26.

Figure 3:
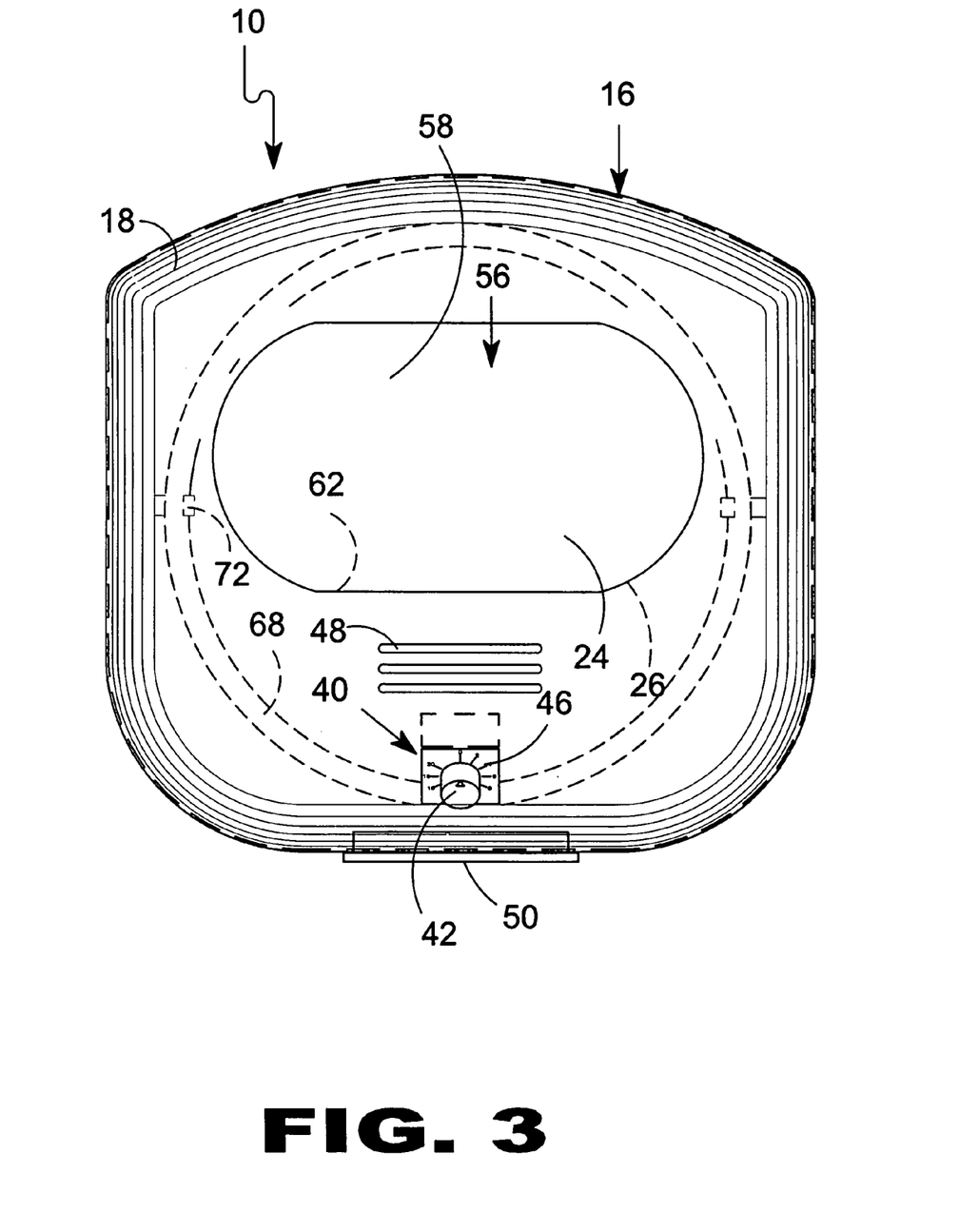
FIG. 3 is a top view of the present invention.

Referring to FIG. 3, shown is a top view of tanning device 10. The tanning device housing 16 has exterior surface 18 with control mechanism 40 mounted thereto. The control mechanism provides the user means for energizing the tanning device for a period of time by selecting a time 46 using timer 42. The user places their feet into a transparent receptacle 56 having aperture 58.

Figure 4:
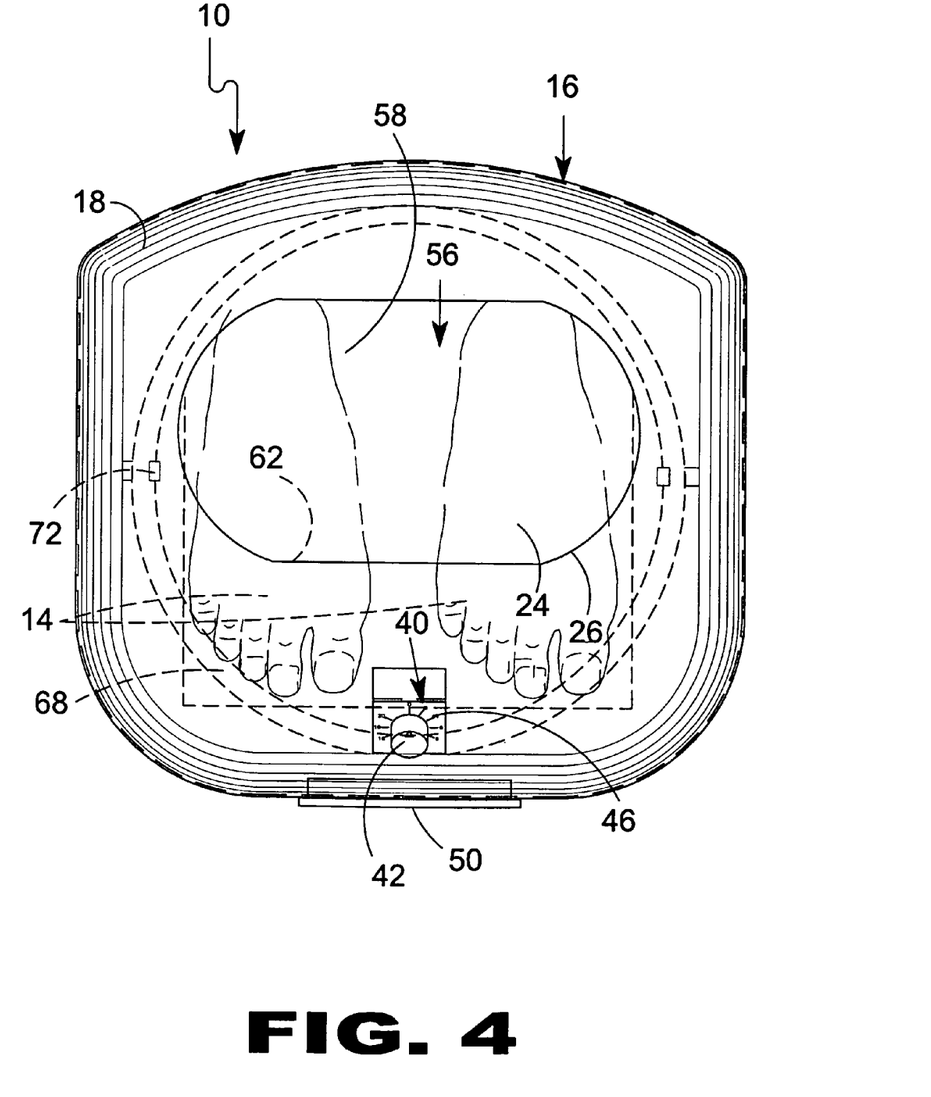
FIG. 4 is a top view of tanning device having a user's feet positioned therein.

Referring to FIG. 4, shown is a top view of tanning device 10 having a user's feet 14 positioned therein. The tanning device housing 16 has exterior surface 18 with control mechanism 40 mounted thereto whereby the user selects the tanning session duration by selecting a time 46 using timer 42 which energizes the ultraviolet light 68 for the selected time period. The user places their feet into the transparent receptacle 56 through aperture 58 which is positioned within housing 16. The transparent receptacle 56 provides adequate space to allow the user to position the feet to allow exposure to all sides of the foot.

Figure 5:
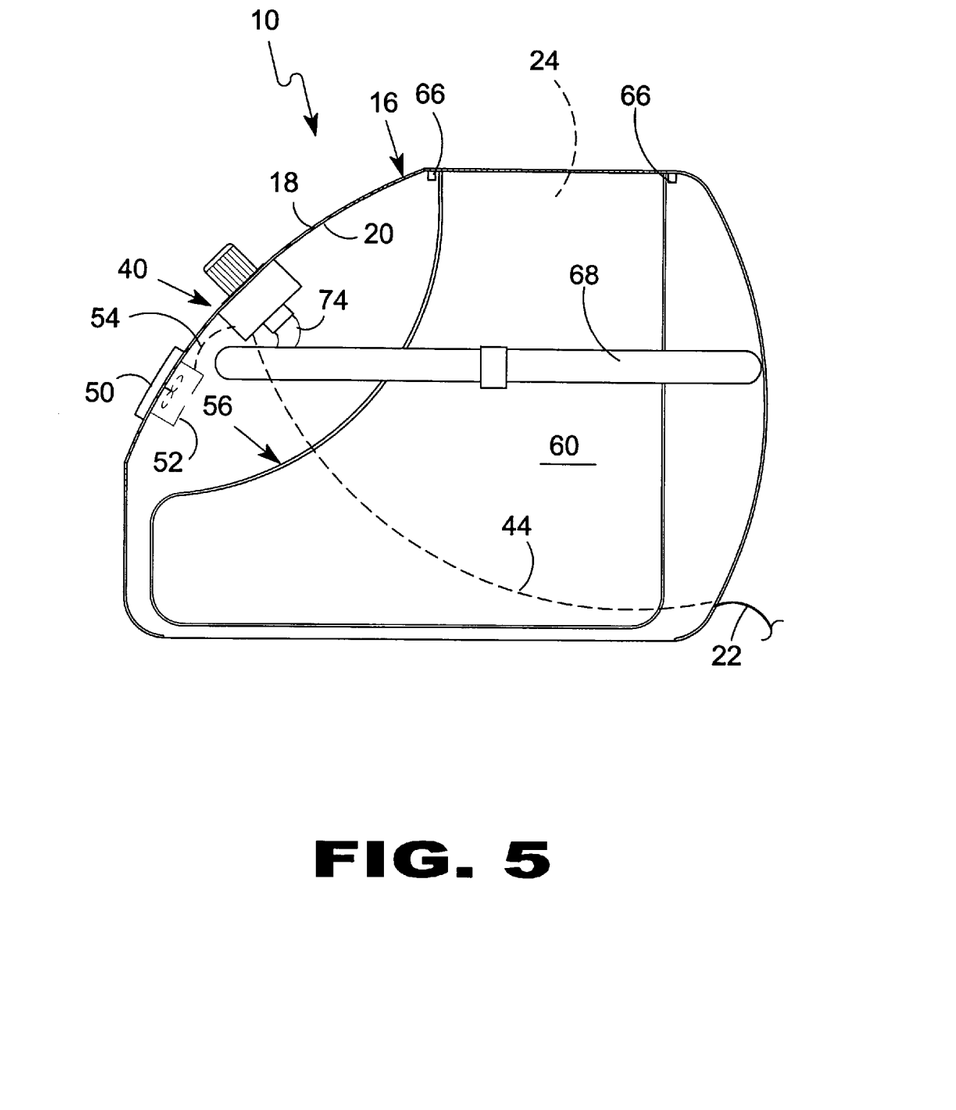
FIG. 5 is an illustrative side view of the tanning device of the present invention.

Referring to FIG. 5, shown is an illustrative side view of the tanning device 10 of the present invention. The housing 16 has an exterior surface 18 with control mechanism 40 mounted thereto that provides the user with means for controlling the duration of the tanning session. Control mechanism 40 has electrical connection 44 with tanning device power source 22 whereby the user selects the duration of the tanning session. Once energized the control mechanism 40 having electrical connection with ultraviolet light 68 and fan 52 controls the duration of the tanning session. The ultraviolet light 68 encompasses transparent receptacle 56 having chamber 60 containing a user's feet. The transparent receptacle forms a clear plastic liner that is a separate compartment for the feet and protects the feet from the lamp(s). In addition the transparent receptacle 56 is removable for external cleaning and sterilization. Because the tanning lamp 68 is circular the tanning device provides an even exposure to the ultraviolet rays. The tanning lam may have a reflective surface on a portion of it to increase the amount of light directed at the feet.

Figure 6:
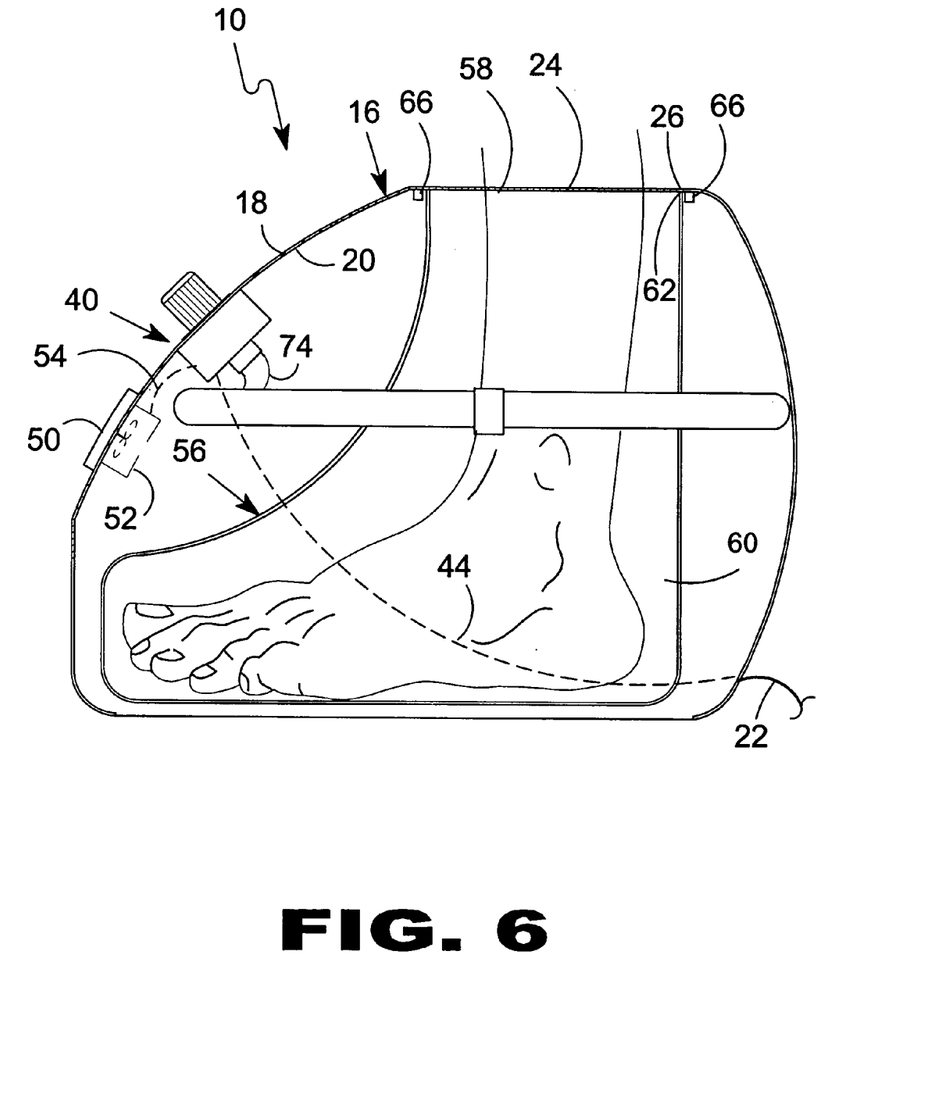
FIG. 6 is a side view of the tanning device of the present invention having a user's feet positioned therein.

Referring to FIG. 6, shown is a side view of the tanning device 10 of the present invention having a user's 12 feet 14 positioned therein. The housing 16 has an exterior surface 18 with control mechanism 40 mounted thereto whereby the user controls the duration of the tanning session. Once the time duration of the control mechanism 40 has been selected the timer 42 having electrical connection 44 with the tanning device power source 22 energizes ultraviolet light 68 and fan 52 for the duration of the tanning session. The ultraviolet light 68 which peripherally encompasses the transparent receptacle 56 having the user's feet 14 within chamber 60 containing provides the ultraviolet rays for the tanning session. The transparent receptacle 56 is a clear member forming a separate compartment for the feet and protects the feet from the lamp(s).

Figure 7:
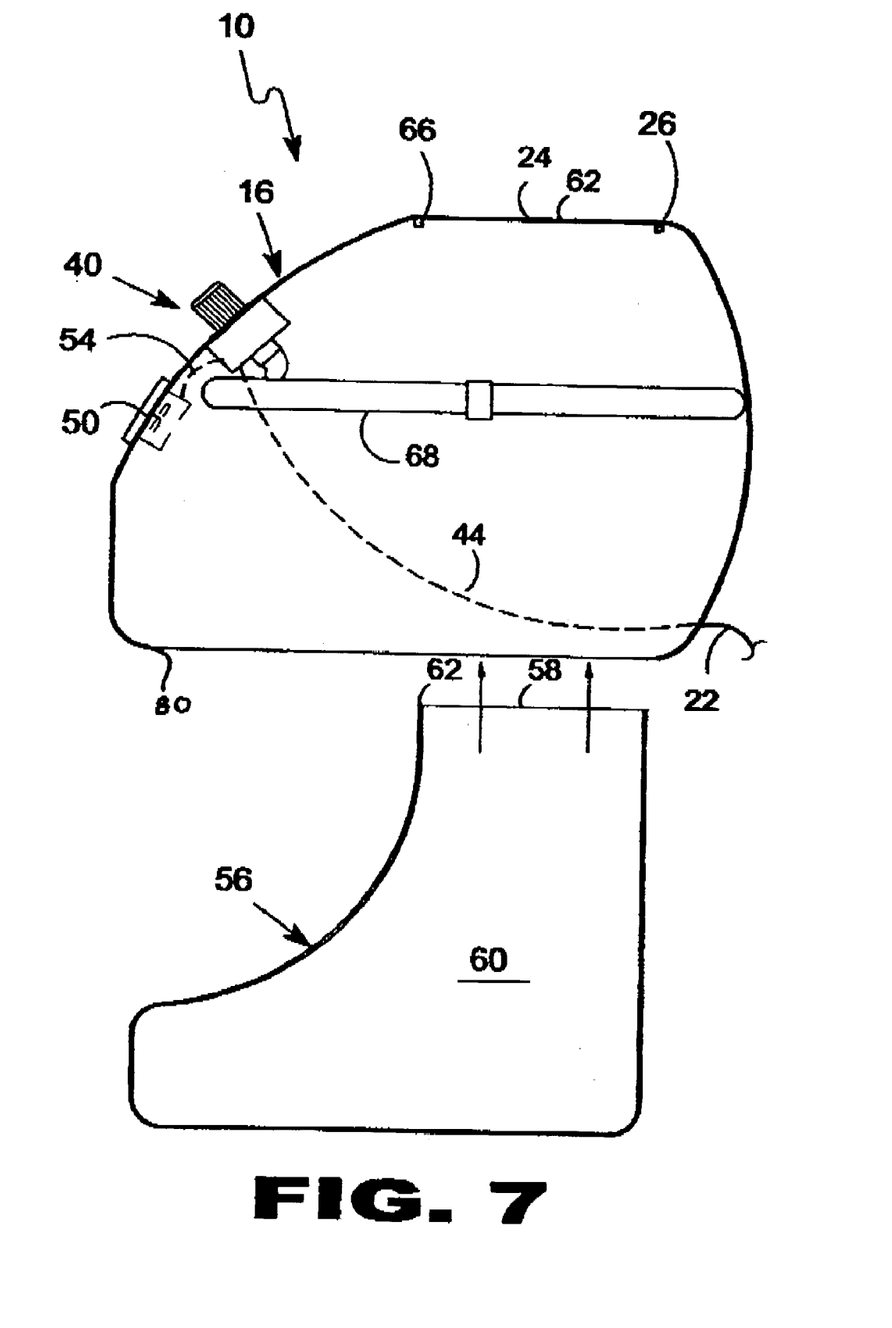
FIG. 7 is a side view of the portable tanning device with the transparent foot receptacle removed.

Referring to FIG. 7, shown is a side view of the portable tanning device 10 with transparent foot receptacle 56 removed. As clearly illustrated in this figure, receptacle 56 is inserted into and removed from device 10 through an opening 80 in the bottom. The present invention is an enclosure with an electrical powered circular tanning lamp 68 that enables a person to tan a portion of the body using control mechanism 40. The lamp 68 is isolated within the enclosure to prevent the skin 14 from contacting the lamp 68.

What is claimed is new and desired to be protected by Letters Patent is set forth in the appended claims:

1. A portable tanning device comprising:
   a. a housing with an aperture in a top surface thereof for providing access into a chamber within said housing providing means for containing a user's feet and ankles;
   b. an ultraviolet light source mounted within said housing for encircling the feet and ankles during a tanning session;
   c. control means on an outer surface of said housing for controlling duration of the tanning session;
   d. a removable feet retaining receptacle within said chamber having an upper opening for receiving the user's feet and ankles through said aperture in said housing; and
   e. said housing having an opening in a bottom surface thereof for insertion and removal of said removable feet retaining receptacle.

2. The device as recited in claim 1, wherein said feet retaining receptacle is manufactured from a transparent material.

3. The device as recited in claim 2, wherein said feet retaining receptacle is centrally positioned within said chamber with the ultraviolet light source surrounding said feet retaining receptacle.

4. The device as recited in claim 3, whereby removal of said feet retaining receptacle provides access to internal components of the portable tanning device.

5. The device as recited in claim 1, wherein the ultraviolet light source is a substantially circular tube-like bulb.

6. The device as recited in claim 5, wherein said ultraviolet light source is selectively removable from said device through said opening in said bottom surface of said device.

7. The device as recited in claim 1, wherein said control means has a movable switch for varying the length of time of a tanning session.

8. The device as recited in claim 7, wherein said control means includes a timer with indicia providing means for determining and energizing the tanning device for a predetermined period of time.

9. The device as recited in claim 8, wherein said control means is electrically connected to an external power source.

10. The device as recited in claim 9, wherein said control means is electrically connected to an ultraviolet light source.

11. The device as recited in claim 10, wherein said control means is electrically connected to a fan wherein said fan is energized by said timer.

12. The device as recited in claim 11, wherein said tanning device housing has at least one vent providing a source of ambient air for said fan.

13. The device as recited in claim 12, having a second vent and wherein said tanning device has an additional fan wherein a volumetric exhaust of air is increased due to said second vent.

* * * * *